(12) United States Patent
Wood

(10) Patent No.: US 9,326,684 B2
(45) Date of Patent: May 3, 2016

(54) MAGNETIC ENHANCEMENT IN DETERMINATION OF PHYSIOLOGICAL BLOOD PARAMETERS

(75) Inventor: Lockett E. Wood, Lyons, CO (US)

(73) Assignee: Covidien LP, Mansfield, MA (US)

( * ) Notice: Subject to any disclaimer, the term of this patent is extended or adjusted under 35 U.S.C. 154(b) by 213 days.

(21) Appl. No.: 13/291,751

(22) Filed: Nov. 8, 2011

(65) Prior Publication Data

US 2013/0116519 A1     May 9, 2013

(51) Int. Cl.
| | | |
|---|---|---|
| A61B 5/1455 | (2006.01) | |
| A61B 5/00 | (2006.01) | |
| A61B 5/055 | (2006.01) | |

(52) U.S. Cl.
CPC ............ *A61B 5/0059* (2013.01); *A61B 5/1455* (2013.01); *A61B 5/055* (2013.01); *A61B 5/6816* (2013.01); *A61B 5/6826* (2013.01); *A61B 5/6828* (2013.01)

(58) Field of Classification Search
CPC .. A61B 5/1455; A61B 5/14551; A61B 5/002; A61B 5/0059; A61B 5/145; A61B 5/14532
USPC ........ 600/309, 310, 322, 323, 324, 326, 328, 600/333, 340, 344, 473, 476, 407, 421, 600/410; 356/41
See application file for complete search history.

(56) References Cited

U.S. PATENT DOCUMENTS

| | | | |
|---|---|---|---|
| 5,273,041 A * | 12/1993 | Richards et al. ............. | 600/411 |
| 5,311,135 A * | 5/1994 | Vavrek et al. ................ | 324/318 |
| 5,323,776 A * | 6/1994 | Blakeley et al. .............. | 600/324 |
| 5,413,100 A | 5/1995 | Barthelemy et al. | |
| 5,555,855 A | 9/1996 | Takahashi | |
| 5,630,413 A * | 5/1997 | Thomas et al. ............... | 600/310 |
| 6,058,324 A | 5/2000 | Chance | |
| 6,192,260 B1 | 2/2001 | Chance | |
| 6,246,892 B1 | 6/2001 | Chance | |
| 6,640,116 B2 * | 10/2003 | Diab ............................ | 600/322 |
| 7,239,904 B2 * | 7/2007 | Hirao ................ | A61B 5/14558 600/316 |
| 2007/0060807 A1 * | 3/2007 | Oishi .......................... | 600/322 |
| 2008/0139908 A1 | 6/2008 | Kurth | |
| 2009/0318784 A1 * | 12/2009 | Newman et al. ............. | 600/309 |
| 2011/0071373 A1 | 3/2011 | Li et al. | |

FOREIGN PATENT DOCUMENTS

| | | |
|---|---|---|
| RU | 2038037 | 6/1995 |
| RU | 2040912 | 8/1995 |

OTHER PUBLICATIONS

Higashi et al., "Orientation of erythrocytes in a strong static magnetic field", Blood, vol. 82, No. 4 Aug. 15, 1993: pp. 1328-1334.*

(Continued)

*Primary Examiner* — Eric Winakur
*Assistant Examiner* — Chu Chuan (JJ) Liu

(57) ABSTRACT

Systems and methods for measuring a physiological parameter of blood in a patient are provided herein. An example method includes establishing with a magnetic array, an first magnetic field along tissue of the patient inserted into the magnetic array and a second magnetic field perpendicular to the tissue, emitting optical signals into further tissue of the patient during at least a first alignment of the magnetic array around the tissue, detecting characteristics of the optical signals, and identifying a value of a physiological parameter based on at least the characteristics of the optical signals.

17 Claims, 10 Drawing Sheets

(56) References Cited

OTHER PUBLICATIONS

Motta, "High magnetic field effects on human deoxygenated hemoglobin light absorption", Bioelectrochemistry and Bioenergetics 47 (1998), 297-300.*

PhysicsTutorials, http://www.physicstutorials.org/home/magnetism/magnetic-field-around-a-solenoid, Apr. 13, 2011.*

Vasilis Ntziachristos, et al.; "Oximetry Based on Diffuse Photon Density Wave Differentials;" Medical Physics; Feb. 2000; pp. 410-421; vol. 27, No. 2; Am. Assoc. Phys. Med.; Melville, NY, US.

* cited by examiner

MAGNETIC ENHANCEMENT IN DETERMINATION OF PHYSIOLOGICAL BLOOD PARAMETERS

TECHNICAL FIELD

Aspects of the disclosure are related to the field of medical devices, and in particular, measuring physiological parameters of blood based on optical signals emitted into tissue while applying magnetic fields.

TECHNICAL BACKGROUND

Various devices, such as pulse oximetry devices, can measure some parameters of blood flow in a patient, such as heart rate and oxygen saturation of hemoglobin. Pulse oximetry devices are a non-invasive measurement device, typically employing solid-state lighting elements, such as light-emitting diodes (LEDs) or solid state lasers, to introduce light into the tissue of a patent. The light is then detected and analyzed to determine the parameters of the blood flow in the patient. However, conventional pulse oximetry devices typically only measure certain blood parameters, and are subject to patient-specific noise and inconsistencies which limits the accuracy of such devices.

Magnetic alignment of blood components, such as erythrocytes, can be achieved in tissue. However, the magnetic field strengths typically required for statistically significant alignment of blood components are extremely high. Magnetic field strengths upwards of 2-4 Teslas are typically required, and difficult to achieve with conventional magnets or in a clinical environment. Superconducting magnetic elements are typically required to achieve such large field strengths, and are extremely bulky precluding easy measurement of tissue such as a fingertip. Moreover, the magnetic fields produced by typical magnetic devices are in a single direction, preventing desired alignments of blood components.

Overview

Systems and methods for measuring a physiological parameter of blood in a patient are provided herein. In a first example, a system for measuring a physiological parameter of blood in a patient is provided. The system includes a magnetic array configured to have tissue of the patient inserted therein, and establish an axial magnetic field along a first portion of the tissue and a radial magnetic field perpendicular to the first portion of the tissue. The system also includes a transceiver module configured to emit a first optical signal into a second portion of the tissue during an initial alignment of the magnetic array, and emit a second optical signal into the second portion of the tissue during a rotated alignment of the magnetic array. The transceiver module is also configured to detect characteristics of the first optical signal and the second optical signal. The system also includes a processing module configured to identify a value of a physiological parameter based on at least the characteristics of the first optical signal and the second optical signal.

In another example, a method for measuring a physiological parameter of blood in a patient is provided. The method includes establishing with a magnetic array, an axial magnetic field along tissue of the patient inserted into the magnetic array and a radial magnetic field perpendicular to the tissue, emitting optical signals into further tissue of the patient during at least a first alignment of the magnetic array around the tissue, detecting characteristics of the optical signals, and identifying a value of a physiological parameter based on at least the characteristics of the optical signals.

In another example, a system for measuring a physiological parameter of blood in a patient is provided. The system includes a magnetic array comprising an central hole configured to have a digit of the patient inserted therein, the magnetic array configured to simultaneously establish within the central hole a first magnetic field along the length of an inserted digit and a second magnetic field perpendicular to the inserted digit. The system also includes a transceiver module configured to emit a first optical signal into tissue of the digit during an initial alignment of the magnetic array around the inserted digit, and emit a second optical signal into the tissue of the digit during a rotated alignment of the magnetic array around the inserted digit. The transceiver module is also configured to detect characteristics of the first optical signal and the second optical signal through the tissue of the digit. The system also includes a processing module configured to identify a value of a physiological parameter based on at least the alignment of the magnetic array and the characteristics of the first optical signal and the second optical signal.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views. While several embodiments are described in connection with these drawings, the disclosure is not limited to the embodiments disclosed herein. On the contrary, the intent is to cover all alternatives, modifications, and equivalents.

DETAILED DESCRIPTION

Various physiological parameters of blood in a patient, such as total hemoglobin (tHb) can be difficult to measure by non-invasive means. Components of blood, such as red blood cells, also called erythrocytes, carry hemoglobin in the blood. These erythrocytes also exhibit magnetic sensitivity, namely anisotropic diamagnetic susceptibility, and will align with strong magnetic fields independent of a state of oxygenation of the hemoglobin. When no magnetic field is applied to tissue, these erythrocytes are randomly oriented within the blood. When randomly oriented, light projected through tissue is scattered randomly and has any detected optical signals have low signal-to-noise ratios, reducing the effectiveness of measurement of these physiological parameters. Light that does reach an optical detector during random orientation of erythrocytes is typically scattered many times and attenuated before detection. An applied magnetic field can modify the scattering coefficient of hemoglobin and thereby modulate optical or other signals detected by non-invasive means. An applied magnetic field will tend to align the erythrocytes and thus present a much lower cross-section to light parallel to the magnetic field, and a much higher cross section to light perpendicular to the field. The number of erythrocytes aligned is typically proportional to the applied magnetic field strength. However, in magnetic fields of 4 Telsas and above, almost all erythrocytes are aligned to the field, greatly reducing the randomness of the erythrocytes. Also, measurement of total hemoglobin is greatly enhanced by use of a two-dimensional magnetic field applied to the tissue, where the two-dimensional magnetic field observed in the tissue has a first observed magnetic field component orthogonal to a second observed magnetic field component.

Figure 1:
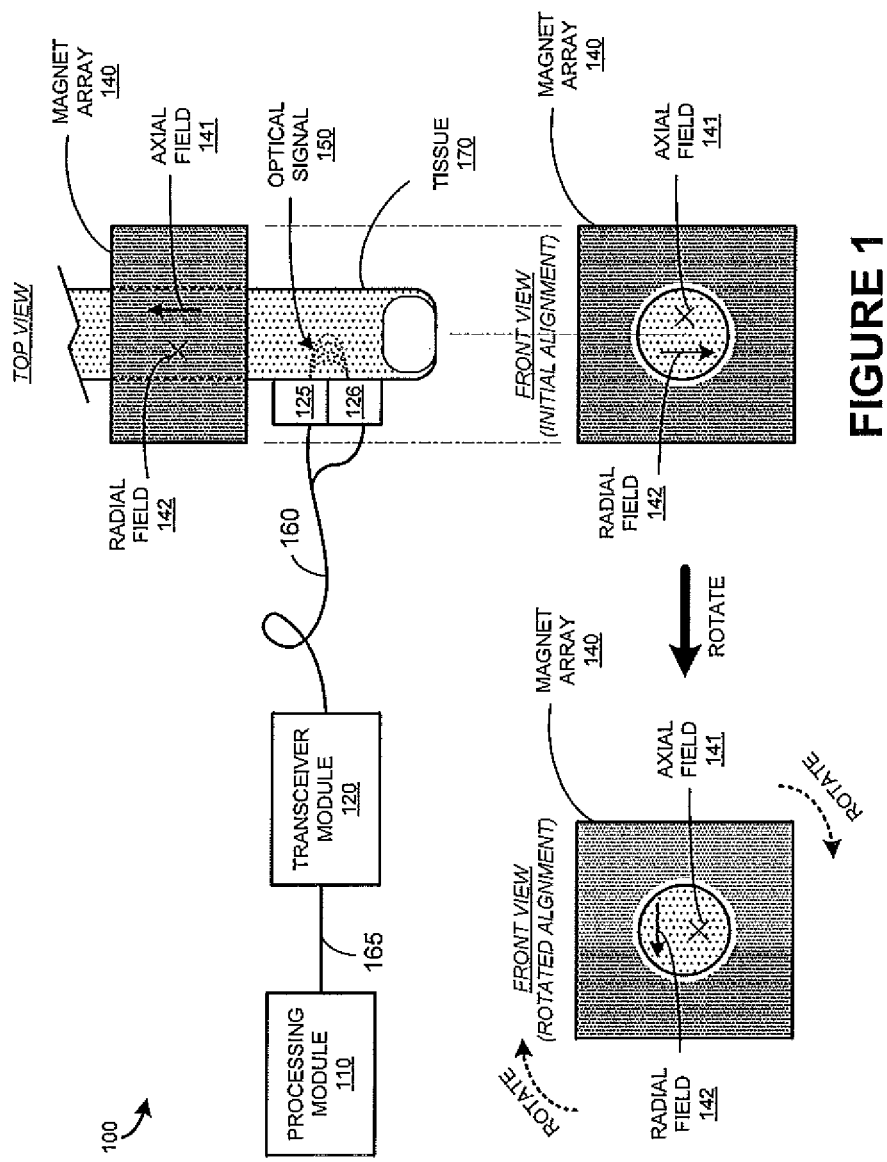
FIG. 1 is a system diagram illustrating a system for measuring a physiological parameter of blood in a patient.

As a first example of a system for measuring a physiological parameter of blood in a patient, FIG. 1 is presented. FIG. 1 illustrates system 100, which includes processing module 110, transceiver module 120, emitter 125, detector 126, magnet array 140, and tissue 170. Processing module 110 and transceiver module 120 communicate over link 165. Transceiver module 120 communicates with emitter 125 and detector 126 over link 160.

In FIG. 1, tissue 170 is inserted through a central hole in magnet array 140. Tissue 170 comprises tissue of a patient, such as a finger, toe, arm, leg, earlobe, or other tissue portion of a patient. Magnet array 140 forms two separate magnetic fields within the central hole, and thus the inserted portion of tissue 170 observes a two-dimensional magnetic field. In FIG. 1, the two-dimensional magnetic field has a first vector component shown as axial field 141 and a second vector component shown as radial field 142. Axial field 141 is typically along the length of the tissue, and radial field 142 is typically across the tissue. Axial field 142 could also be referred to as a longitudinal field. While magnet array 140 has tissue inserted therein, optical signal 150 is applied by emitter 125 into tissue 170. Detector 126 detects optical signal 150 which has been transmitted, reflected, or scattered through tissue 170.

Tissue 170 is a portion of the tissue of a patent undergoing measurement of a physiological blood parameter, and is represented by a cylindrical element for simplicity herein. Although the term 'optical' or 'light' is used herein for convenience, it should be understood that the measurement signals are not limited to visible light, and could comprise any photonic, electromagnetic, or energy signals, such as visible, infrared, ultraviolet, radio, or other signals. The wavelength of light applied to the tissue can be selected based on many factors, such as optimized to a wavelength strongly absorbed by hemoglobin. When a suitable magnetic field is applied to the tissue and rotated, the variation of detected light, or other applied signal such as sound, is proportional to the number of erythrocytes in the tissue. Tissue components such as lipids, proteins, or trans-membrane proteins, may orient opposite to erythrocyte components under the same magnetic field, and thus these components could be detected in a similar manner using other optical wavelengths which these components absorb.

Figure 2:
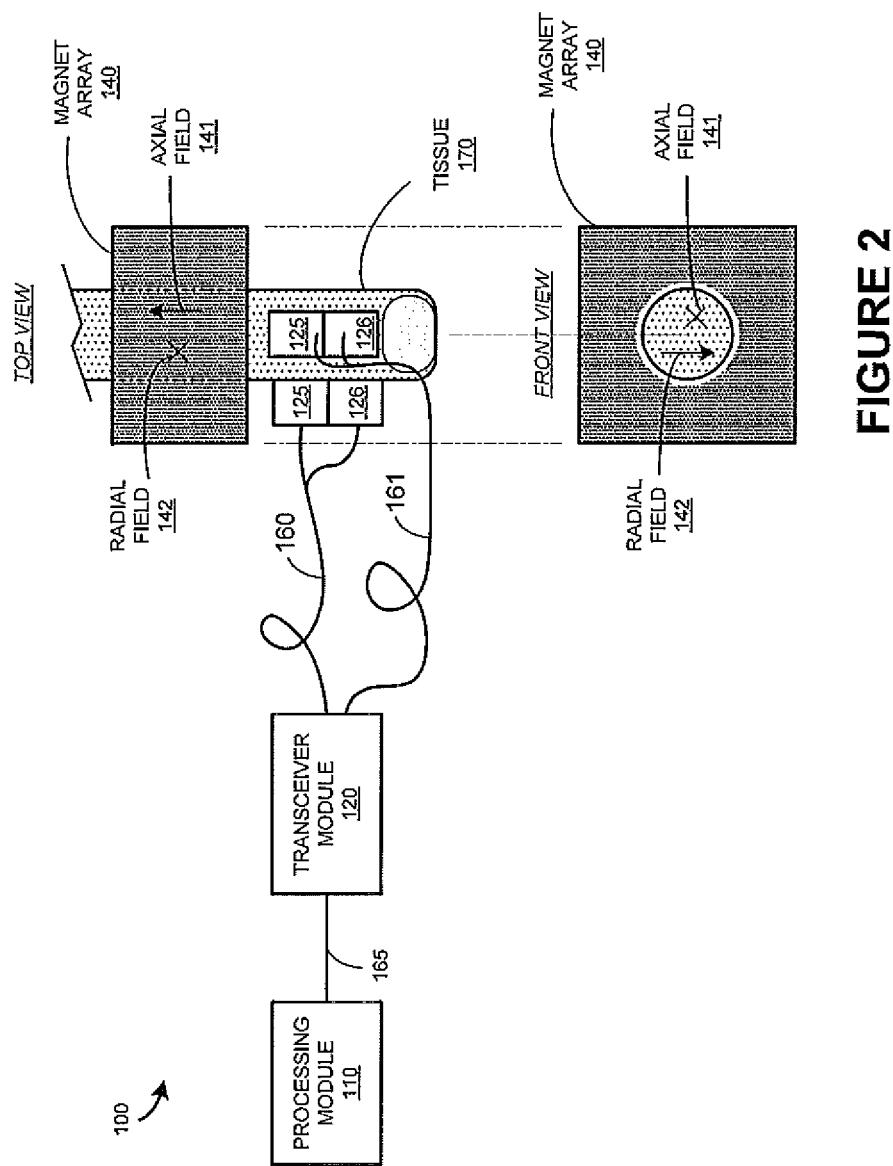
FIG. 2 is a system diagram illustrating a system for measuring a physiological parameter of blood in a patient.

FIG. 2 is a system diagram illustrating a further configuration of system 100 for measuring a physiological parameter of blood in a patient. FIG. 2 includes similar elements as FIG. 1, but also includes a second set of emitter/detector 125/126 with an associated link 161 to communicate with transceiver module 120. A first emitter/detector pair in FIG. 2 is coupled to a first side of tissue 170, and a second emitter/detector pair is coupled to a second side of tissue 170. Thus, the two emitter/detector pairs are oriented orthogonally to each other, where one pair emits/detects first optical signals in a first direction in tissue 170, and another pair emits/detects second optical signals in a second direction in tissue 170. Other orientations and couplings are possible, and this orthogonal positioning of FIG. 2 is merely exemplary. Similar results can also be obtained by using one emitter and two orthogonal detectors or by using one detector and two orthogonal emitters.

Figure 3:
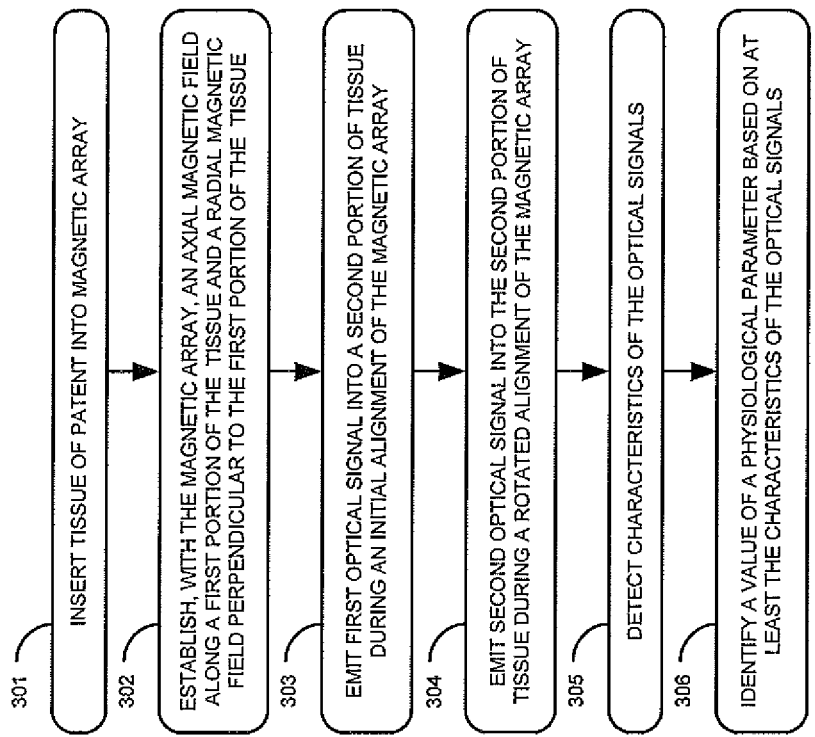
FIG. 3 is a flow diagram illustrating a method of operation of a system for measuring a physiological parameter of blood in a patient.

FIG. 3 is a flow diagram illustrating a method of operation of system 100 for measuring a physiological parameter of blood in a patient. The operations of FIG. 3 are referenced herein parenthetically. In FIG. 3, tissue of a patient is inserted (301) into a magnetic array. As shown in FIG. 1, tissue 170 is inserted through a central hole in magnet array 140. Magnet array 140 could slip over a portion of tissue 170, similar to how a ring or band would slip over a finger or toe of a patient. In other examples, magnet array 140 includes a hinged element for forming a clamshell configuration to have tissue 170 inserted into the central hole.

Magnet array 140 establishes (302) axial magnetic field 141 along a first portion of tissue 170 and radial magnetic field 142 across or perpendicular to the first portion of tissue 170. As shown in FIG. 1, the "top view" illustrates axial field 141 directed along the length of tissue 170 and radial field 142 downward into tissue 170 and shown by associated vector representations directed up and directed away from the reader. Other vector representations and field configurations could be employed; however, a two-field configuration is preferred in this example.

Transceiver module 120 emits (303) a first optical signal into a second portion of tissue 170 during an initial alignment of the magnetic array. In this example, the first optical signal is transferred by transceiver module 120 over link 160. Emitter 125 then emits the first optical signal into tissue 170. In some examples, transceiver module 120 emits an optical signal for transfer over an optical fiber portion of link 160 and subsequent emission into tissue 170. In other examples, an electronic signal is transferred over link 160 by transceiver module 120, and emitter 125 converts the electronic signal into the first optical signal for emission into tissue 170.

The initial alignment of magnet array 140 includes a first rotational positioning of magnet array 140 around tissue 170. As a typical example, FIG. 1 shows an initial alignment and a rotated alignment in the two "front view" portions of FIG. 1. The initial alignment view illustrates the alignment of the magnetic field components for an initial angular configuration. Specifically, the initial alignment includes a downward vector for radial magnetic field 142 and an inward vector for axial magnetic field 141.

Transceiver module 120 emits (304) a second optical signal into the second portion of tissue 170 during a rotated alignment of the magnetic array. In this example, the second optical signal is transferred by transceiver module 120 over link 160. Emitter 125 then emits the second optical signal into tissue 170. In some examples, transceiver 120 emits an optical signal for transfer over an optical fiber portion of link 160 and subsequent emission into tissue 170. In other examples, an electronic signal is transferred over link 160 by transceiver module 120, and emitter 125 converts the electronic signal into the second optical signal for emission into tissue 170.

The rotated alignment of magnet array 140 includes a second rotational positioning of magnet array 140 around tissue 170. The rotated alignment could be achieved by changing the rotational configuration between magnet array 140 and tissue 170 by 90 degrees clockwise. Other rotational directions and magnitudes could be employed. As a typical example, FIG. 1 shows an initial alignment and a rotated alignment in the two "front view" portions of FIG. 1. The rotated alignment view illustrates the alignment of the magnetic field components under a rotated angular configuration. Specifically, the rotated alignment includes a leftward vector for radial magnetic field 142 and an inward vector for axial magnetic field 141. Thus, magnet array 140 has been rotated from the initial alignment to the rotated alignment, and radial field 142 will have changed direction by 90 degrees, while axial field 141 will have remained unchanged in direction.

Transceiver module 120 detects (305) characteristics of the optical signals. In this example, the first optical signal and the second optical signal are detected by transceiver module 120 over link 160. Detector 126 captures light related to the first optical signal and the second optical signal as transmitted, reflected, or scattered through tissue 170. In some examples, transceiver module 120 comprises a photodetector portion which receives the light captured by detector 126 over an optical fiber portion of link 160, and transceiver module 120 converts optical characteristics of the optical signals into electronic signals. In other examples, detector 126 comprises a photodetector portion to receive the optical signals from tissue 170, and detector 126 converts optical characteristics of the optical signals into electronic signals for transfer over link 160.

In this example, the first optical signal is applied to tissue 170 during the initial alignment of magnet array 140, while the second optical signal is applied to tissue 170 during the rotated alignment of magnet array 140. During application of the first optical signal into tissue 170, transceiver module 120 detects the first optical signal transferred through tissue 170. Likewise, during application of the second optical signal into tissue 170, transceiver module 120 detects the second optical signal transferred through tissue 170. Magnetically sensitive components of tissue 170 will react to the initial alignment of magnet array 140 and to the rotated alignment of magnet array 140. The magnetically sensitive components could include blood components, such as erythrocytes. These magnetically sensitive tissue components will tend to align along the magnetic fields produced by magnet array 140. Since magnet array 140 produces a two-dimensional magnetic field, namely the axial and radial fields, the tissue components will align according to the applied two-dimensional magnetic field. When magnet array 140 is rotated, and thus the applied magnetic field is altered, the tissue components will likewise align according to the rotated two-dimensional magnetic field.

Processing module 110 identifies (306) a value of a physiological parameter based on at least the characteristics of the optical signals. The physiological parameter could include any parameter associated with blood or tissue 170 of the patient, such as total hemoglobin concentration (tHb), regional oxygen saturation (rSO2), or arterial oxygen saturation (SpO2), among other parameters, including combinations thereof. The characteristics of the optical signals could include an amplitude or intensity of detected optical signals through tissue 170. The characteristics could also include a phase delay of the optical signals if a reference optical signal is employed. Since two alignments of magnet array 140 are employed in this example, measurements of the characteristics are taken during each alignment. The characteristics of the optical signals at each alignment could then be processed to determine the physiological parameter. In some examples, a ratio or differential of the characteristics or associated values for each alignment could be processed to determine the value of the physiological parameter. In further examples, the rotational angle of magnet array 140, angular relationship between the emitter/detector and magnet array 140, or other relationships are also processed along with the characteristics of the optical signals to determine the value of the physiological parameter.

Figure 4:
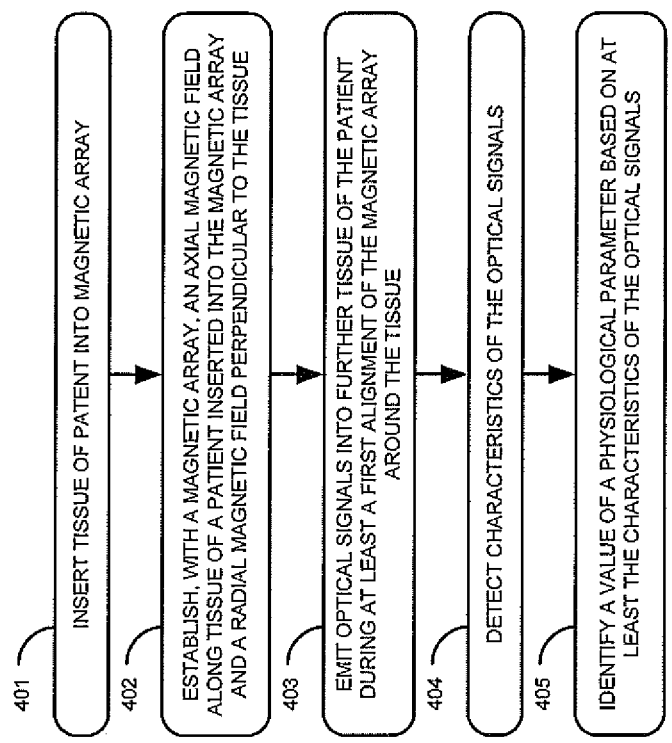
FIG. 4 is a flow diagram illustrating a method of operation of a system for measuring a physiological parameter of blood in a patient.

FIG. 4 is a flow diagram illustrating a further method of operation of system 100, as found in FIG. 2, for measuring a physiological parameter of blood in a patient. The operations of FIG. 4 are referenced herein parenthetically. In FIG. 4, tissue of a patient is inserted (401) into a magnetic array. As shown in FIG. 2, and likewise similar to FIG. 1, tissue 170 is inserted through a central hole in magnet array 140. Magnet array 140 could slip over a portion of tissue 170, similar to how a ring or band would slip over a digit of a patient. In other examples, magnet array 140 includes a hinged element for forming a clamshell configuration to have tissue 170 inserted into the central hole.

Magnet array 140 establishes (402) axial magnetic field 141 along a portion of tissue 170 and radial magnetic field 142 perpendicular to the portion of tissue 170. As shown in FIG. 2, the "top view" illustrates axial field 141 directed along the length of tissue 170 and radial field 142 downward into tissue 170 and shown by associated vector representations directed up and directed away from the reader. Other vector representations and field configurations could be employed; however, a two-field configuration is preferred in this example.

Transceiver module 120 emits (403) optical signals into a further portion of tissue 170 during a measurement alignment of the magnetic array. As shown in FIG. 2, a first optical signal is transferred over link 160 to a first emitter 125, and a second optical signal is transferred over link 161 to a second emitter 125. The first and second emitter 125 then each emits the associated optical signals into tissue 170. In some examples, transceiver module 120 emits optical signals for transfer over an optical fiber portion of each of links 160-161 and subsequent emission into tissue 170. In other examples, electronic signals are transferred over each of links 160-161 by transceiver module 120, and the first and second emitter 125 each convert the associated electronic signals into optical signals for emission into tissue 170.

The measurement alignment of magnet array 140 includes a rotational positioning of magnet array 140 around tissue 170. As a typical example, FIG. 2 shows measurement alignment in the "front view" portions of FIG. 2. The measurement alignment view illustrates the alignment of the magnetic field components for a particular angular configuration. Specifically, the measurement alignment includes a downward vector for radial magnetic field 142 and an inward vector for axial magnetic field 141. In the example shown in FIG. 2, only a single measurement alignment is employed, and magnet array 140 is not rotated around tissue 170. Also, the pictured measurement alignment shown in FIG. 2 could be at any angular rotation of magnet array 140 around tissue 170.

Transceiver module 120 detects (404) characteristics of the optical signals. In this example, the first optical signal and the second optical signal as emitted by the respective emitters 125 are detected by transceiver module 120 over associated links 160-161. Each detector 126 captures light related to the first optical signal and the second optical signal through tissue 170. In some examples, transceiver module 120 comprises a photodetector portion which receives the light captured by each detector 126 over an optical fiber portion of links 160-161, and transceiver module 120 converts optical characteristics of the optical signals into electrical signals. In other examples, each detector 126 comprises a photodetector portion to receive the optical signals from tissue 170, and each detector 126 converts optical characteristics of the optical signals into electronic signals for transfer over associated links 160-161.

Since two optical signals are emitted and detected in tissue 170 in FIG. 2 by a pair of emitter/detectors, various configurations could be employed to ensure the optical signals of one emitter/detector pair do not interfere with the other emitter/detector pair. For example, one emitter/detector pair could be enabled when the other is disabled, creating a time-sequential measurement of tissue 170. In another example, different characteristics of the optical signals could be employed to ensure separation of the two optical signals from each other, such as different wavelengths, different modulations, or different encodings of the optical signals for each emitter 125. In yet another example, the intensity of the optical signals for each emitter 125 may be reduced to minimize interference due to spatial positioning of each emitter 125.

In this example, optical signals are applied to tissue 170 during the single rotational alignment of magnet array 140. During application of the optical signals into tissue 170, transceiver module 120 detects the optical signals transferred through tissue 170. Magnetically sensitive components of tissue 170 will react to the alignment of magnet array 140. These magnetically sensitive tissue components will tend to align along the magnetic fields produced by magnet array 140. Since magnet array 140 produces a two-dimensional magnetic field, namely the axial and radial fields, the tissue components will align according to the applied two-dimensional magnetic field.

Processing module 110 identifies (405) a value of a physiological parameter based on at least the characteristics of the optical signals. The physiological parameter could include any parameter associated with blood or tissue 170 of the patient, such as total hemoglobin concentration (tHb), regional oxygen saturation (rSO2), or arterial oxygen saturation (SpO2), among other parameters, including combinations thereof. The characteristics of the optical signals could include an amplitude or intensity of detected optical signals through tissue 170. The characteristics could also include a phase delay of optical signal if modulated optical signals are employed. Since two emitter/detector pairs on tissue 170 are employed in FIG. 2, measurements of the characteristics are taken for each pair. The characteristics of the optical signals at each pair could then be processed to determine the physiological parameter. In some examples, a ratio of the characteristics or associated values for each pair could be processed to determine the value of the physiological parameter. Information related to the positioning of each emitter/detector pair relative to each other and to magnet array 140 could also be processed to determine the physiological parameter, such as an angular relationship, positional offset, or other information.

Figure 5:
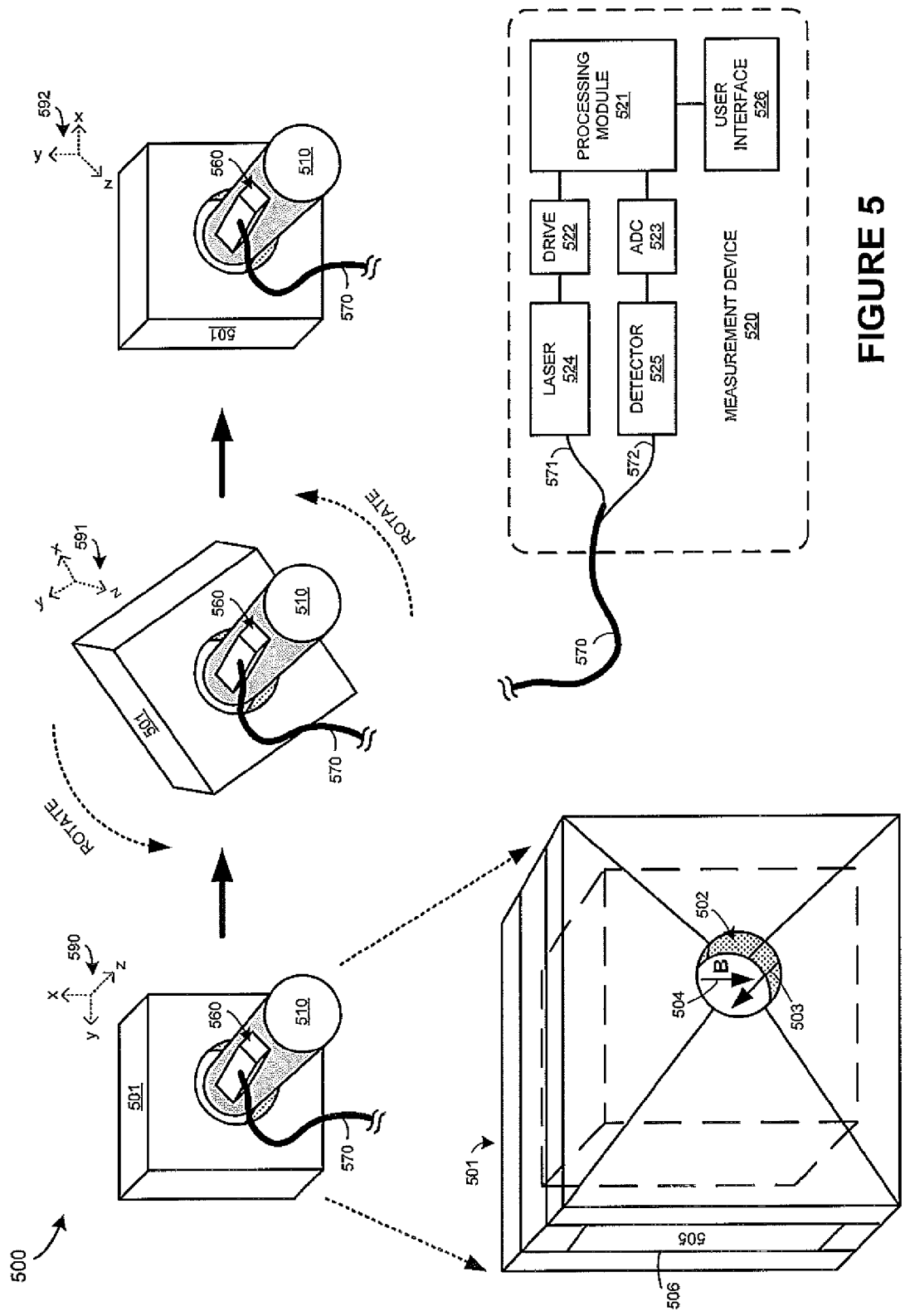
FIG. 5 is a system diagram illustrating a system for measuring a physiological parameter of blood in a patient.

FIG. 5 is a system diagram illustrating system 500 for measuring a physiological parameter of blood in a patient. FIG. 5 includes magnet array 501, finger 510, measurement device 520, and optical coupler 560. Optical coupler 560 and measurement device 520 communicate over link 570. Optical coupler 560 is coupled to finger 510 (shown external to magnet for clarity). In this example, a simplified block is used to represent optical coupler, but in other examples optical coupler could include a clamp, band, adhesive, or other coupling mechanism to hold optical coupler 560 onto finger 510. Also, although finger 510 is described in this example, it should be understood that any tissue of a patient could be measured, such as a digit, arm, leg, earlobe, or other tissue. Finger 510 comprises tissue such as blood, capillaries, arteries, veins, fat, muscle, bone, nails, or other biological tissue and associated components.

In FIG. 5, magnet array 501 is initially placed over a finger 510 of a patient undergoing a measurement. A measurement is made during a first rotation of magnet array 501, and then magnet array is rotated around finger 510. Then a second measurement is made during a second rotation of magnet array 501. A three-step sequence is shown in FIG. 5 for clarity. The first step is an illustration of magnet array 501 during a first alignment on finger 510. The second step is an illustration of magnet array 501 during rotation around finger 510. The third step is an illustration of magnet array 501 during a second alignment on finger 510. As shown next to the respective illustration, axes 590-592 each give a further illustration of the angular position of magnet array around finger 510. Specifically, in the first illustration, axis 590 shows a first rotational configuration. During rotation in the second illustration, axis 591 shows an intermediate rotational configuration. In the third illustration, axis 592 shows a second rotational configuration. The second rotational configuration is 90 degrees counterclockwise from the first rotational configuration. Further rotations of magnet array 501 could be used.

FIG. 5 also shows a detailed view of magnet array 501 below the first rotational configuration illustration. The detailed view provides further detail on the array configuration for one example embodiment. Further array configurations could be employed. The detailed view of magnet array 501 includes a plurality of individual permanent magnets 505. The plurality of permanent magnets 505 are each joined together at seams 506. Each line in the detailed view of magnet array 501 indicates a seam between a permanent magnet within the array. The dashed lines indicate interior seams between further permanent magnets. When grouped together into the configuration shown in FIG. 5, the array of permanent magnets creates a strong two-dimensional magnetic field within central hole 502. In this example, the field strength 'B' of component 504 in central hole 502 is a minimum of 2 Teslas (T). Also, in this example, the central hole 502 diameter is 2.5 centimeters (cm), and the hole length is 4.0 cm. It should be understood that different field strengths could be employed, as well as different dimensions for the central hole.

Each permanent magnet could comprise ferromagnetic materials such as iron, nickel, cobalt, or alloys of rare earth metals, including combinations thereof. In some examples, the array of permanent magnets is referred to as a Halbach array, where an array of magnets sums and cancels the various individual magnetic fields for the component magnets to create a controlled and directional net magnetic field. However, typical Halbach arrays only create an observed magnetic field in a single direction, and many configurations of Halbach arrays do not allow insertion of tissue of a patient into the observed magnetic field. This permanent magnet array in FIG. 5 may be the preferred embodiment but a dual-field electromagnet or superconducting magnet could also be used to create the required magnetic fields. In examples where an electromagnet is employed, the field or fields created by the electromagnet could be rotated electronically while keeping the electromagnet physically stationary, thus establishing operation similar to a physically rotating electromagnet.

Central hole 502 is where tissue of a patient is inserted, such as finger 510. Within central hole 502 a two-dimensional magnetic field is observed. A first component of the two-dimensional magnetic field is shown as component 503, and a second component is shown as component 504. In this example, component 503 is shown in the negative 'z' direction referenced to axis 590, and component 504 is shown in the negative 'x' direction referenced to axis 590. It should be understood that the magnetic components and associated 2-D magnetic field stay fixed in orientation with respect to magnet array 501. Thus, as magnet array 501 is rotated around finger 510, the magnetic fields will change direction with respect to finger 510. The associated axes 591-592 illustrate which way the magnetic fields will be directed in subsequent rotational configurations, as referenced back to the initial alignment of axis 590.

FIG. 5 also includes measurement device 520. Measurement device 520 includes components and equipment to emit optical signals into finger 510 and detect the optical signals as scattered through tissue of finger 510. Measurement device 520 includes processing module 521, drive module 522, analog-to-digital converter (ADC) 523, laser 524, detector 525, and user interface 526. Link 570 includes optical links 571-572, such as optical fibers, for communicating optical signals between optical coupler 560 and measurement device 520. Link 571 is used for transmitting optical signals from laser 524 to optical coupler 560 and subsequently into tissue of finger 510. Link 572 is used for receiving optical signals scattered through tissue of finger 510 from optical coupler 560 for detection by detector 525. Various other links within measurement device 520 are used for communicating signals between the various components thereof. These links could comprise optical links, electrical links, wireless links, and could further comprise wires, printed circuit traces, waveguides, or other media. Various communication protocols could be employed over each associated link, such as Controller Area Network (CAN) bus, Inter-Integrated Circuit (I2C), 1-Wire, Radio Frequency Identification (RFID), optical, circuit-switched, Internet Protocol (IP), Ethernet, Wireless Fidelity (WiFi), Bluetooth, communication signaling, or some other communication format, including combinations, improvements, or variations thereof.

Processing module 521 retrieves and executes software or other instructions to direct the operations of the other components of measurement device 520 or optical coupler 560, as well as process data received from ADC 523. In this example, processing module 521 comprises a digital signal processor (DSP), and could include a non-transitory computer-readable medium such as a disk, integrated circuit, server, flash memory, or some other memory device, and also may be distributed among multiple memory devices. Examples of processing system 521 include DSPs, micro-controllers, field programmable gate arrays (FPGA), or discrete logic, including combinations thereof. In one example, the DSP comprises an Analog Devices Blackfin® device.

Drive module 522 comprises electronic components for generating signals for use by laser 524, as well as receiving instructions from processing module 521 for generating these signals. Drive module 522 produces a signal to instruct laser 524 to output a proper optical signal, and drive 522 instructs laser 524 with parameters such as intensity, amplitude, phase offset, modulation, on/off conditions, or other parameters. Drive module 522 could comprise a signal synthesizer, such as a direct digital synthesis (DDS) component, CD/DVD laser driver components, function generators, or other signal generation components. Drive module 522 could also include filters, delay elements, or other calibration components. In some examples, where multiple lasers are employed, drive module 522 could include an RF switch.

Analog-to-digital converter (ADC) 523 comprises analog to digital converter circuitry. ADC 523 receives the detected information from detector 525, and digitizes the information, which could include digitizing intensity, amplitude, or phase information of optical signals converted into electrical signals by detector 525. The dynamic range, bit depth, and sampling rate of ADC 525 could be selected based on the signal parameters of the optical signals driven by laser 524, such as to prevent aliasing, clipping, and for reduction in digitization noise. ADC 525 could each be an integrated circuit ADC, or be implemented in discrete components. ADC 525 provides digitized forms of information for receipt by processing system 521.

Laser 524 comprises a laser element such as a laser diode, solid-state laser, or other laser device, along with associated driving circuitry. Laser 524 emits coherent light over associated optical fiber 571. In this example, a wavelength of light is associated with laser 524 and likewise optical fiber 571. In other examples, multiple lasers and multiple optical fibers are employed to transfer multiple wavelengths of light into tissue of finger 510. The wavelength of light could be tuned to hemoglobin absorbency, such as 660 nm or 808 nm, although other wavelengths could be used. Laser 524 may modify an intensity of the associated laser light, or modulate the associated laser light based on an input signal received from drive module 522. Optical couplers, cabling, or attachments could be included to optically mate laser 524 to optical fiber 571. Additionally, a bias signal may be added or mixed into the signals received from drive module 522, such as adding a "DC" bias for the laser light generation components.

Detector 525 comprises a light detector element, such as a photodiode, phototransistor, avalanche photo diode (APD), photomultiplier tube, charge coupled device (CCD), CMOS optical sensor, or other optoelectronic sensor, along with associated receiver circuitry such as amplifiers or filters. Detector 525 could also include phase or amplitude detector circuitry. Detector 525 receives light over associated optical fiber 572. Optical couplers, cabling, or attachments could be included to optically mate detector 525 to optical fiber 572. Detector 525 converts the optical signals received over optical fiber 572 to electrical signals for transfer to ADC 523. Detector 525 could also include circuitry to condition or filter the signals before transfer to ADC 523. It should be noted that although in this example optical fiber 571 only carries a particular emitted wavelength of light, input optical fiber 572 can carry any received light from tissue of finger 510, which could include multiple wavelengths or stray light from other light sources. Also, although one detector is shown in FIG. 5, in other examples, multiple detectors could be employed and could be shared between multiple laser sources, such as when the detector employs modulation or multiplexing techniques to detect multiple optical signals from a combined detected light.

User interface 526 includes equipment and circuitry to communicate information to a user of measurement device 520. User interface 526 may include any combination of displays and user-accessible controls and may be part of measurement device 520 as shown or could be a separate patient monitor or multi-parameter monitor. When user interface 526 is a separate unit, user interface 526 may include a processing system and may communicate with measurement device 520 over a communication link comprising a serial port, UART, USB, Ethernet, or wireless link such as Bluetooth, Zigbee or WiFi, among other link types. Examples of the equipment to communicate information to the user could include displays, indicator lights, lamps, light-emitting diodes, haptic feedback devices, audible signal transducers, speakers, buzzers, alarms, vibration devices, or other indicator equipment, including combinations thereof. The information could include raw ADC samples, calculated phase and amplitude information for one or more emitter/detector pairs, blood parameter information, waveforms, summarized blood parameter information, graphs, charts, processing status, patient information, or other information. User interface 526 also includes equipment and circuitry for receiving user input and control, such as for beginning, halting, or changing a measurement process or a calibration process. Examples of the equipment and circuitry for receiving user input and control include push buttons, touch screens, selection knobs, dials, switches, actuators, keys, keyboards, pointer devices, microphones, transducers, potentiometers, non-contact sensing circuitry, or other human-interface equipment.

Although laser 524 and detector 525 are each included in measurement device 520 in FIG. 5, in other examples, laser 524 or detector 525 could be included in optical coupler 560. Shorter optical fibers 571-572 or other waveguides could be employed when laser 524 or detector 525 are integrated into optical coupler 560. In some examples, optical fibers 571-572 are not employed between lasers 525 and tissue of finger 510, and the laser light is introduced directly into the tissue, possibly after associated lenses or tissue interface optics. Furthermore, electrical or RF signaling could be employed between optical coupler 560 and measurement device 520 to drive or receive signals from laser 524 or detector 525 when laser 524 or detector 525 are included in optical coupler 560.

Optical coupler 560 comprises a clamp, band, adhesive, or other mechanical coupling mechanism to hold optical coupler 560 onto finger 510. Also, optical coupler 560 could include optical components to couple light into tissue of finger 510 as well as to receive light scattered through tissue of finger 510. These optical components could include lenses or tissue interface optics. Optical couplers, cabling, or attachments could be included to optically mate optical coupler 560 to link 570 or to individual ones of links 571-571. In further examples, optical coupler 560 includes components associated with laser 524 or detector 525.

FIG. 5 illustrates one possible configuration of a magnet array. Other configurations are possible. For example, a first magnetic array could be established with a central hole for tissue, such as a finger, but only producing a one-dimensional magnetic field within the central hole, such as a radial field. Then, another magnetic element could be butt up against one end of the central hole with a magnetic field orthogonal to the first magnetic array to establish a second one-dimensional field within the central hole, such as an axial field. In yet another example, orthogonal toroid electromagnets could be employed. A first toroid electromagnet with an air gap, creating a "C" shaped configuration could be aligned orthogonally with a second toroid electromagnet with a similar air gap, creating a second "C" shaped configuration. A finger could be inserted into the space created by the two air gaps. However, this configuration would only create a net magnetic field in the tissue in a one-dimensional configuration, even though the magnetic field of two electromagnets is applied simultaneously. The finger or the magnets would then be rotated so as to effect a different orientation of the field on the finger. A light source and detector could be included on faces of the electromagnets at the air gaps so optical signals could be applied to a finger when inserted into a similarly sized air gap. In further examples where an electromagnet is employed, the field or fields created by the electromagnet could be rotated electronically while keeping the electromagnet physically stationary, thus establishing operation similar to a physically rotating electromagnet.

Figure 6:
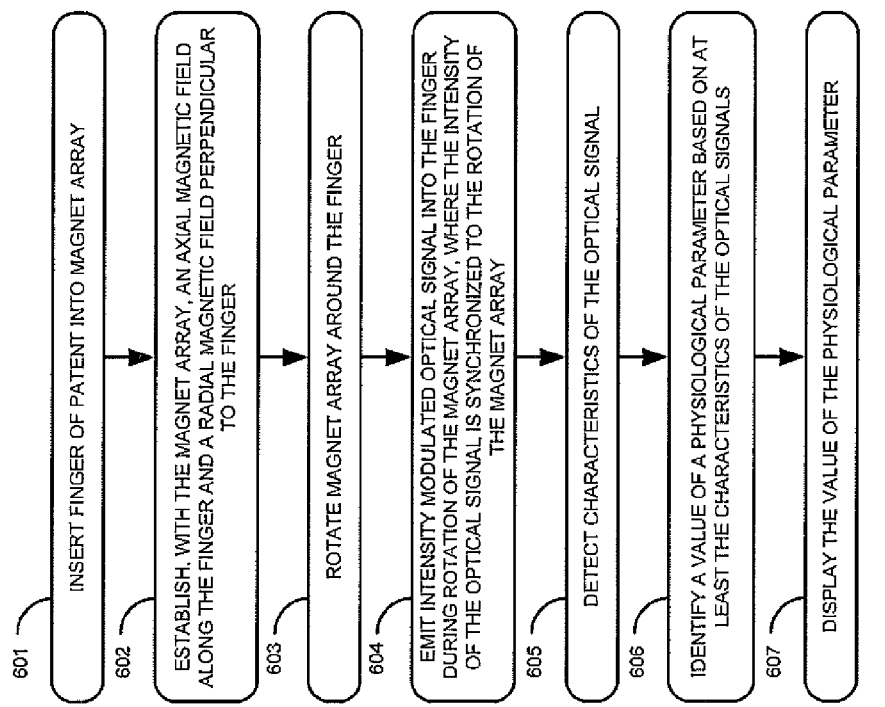
FIG. 6 is a flow diagram illustrating a method of operation of a system for measuring a physiological parameter of blood in a patient.

FIG. 6 is a flow diagram illustrating a method of operation of system 500 for measuring a physiological parameter of blood in a patient. The operations of FIG. 6 are referenced herein parenthetically. In FIG. 6, finger 510 of a patient is inserted (601) into magnet array 501. Finger 510 could be slid into the central hole of magnet array 501 to penetrate the central hole. In other examples, magnet array 501 includes a hinged mechanical design to allow finger 510 to be inserted in a clamshell fashion. Also, in this example, finger 510 is inserted into the central hole of magnet array 501 up to a first insertion distance. The first insertion distance could include a linear distance along finger 510 from the tip of finger 510, or could include a rough positioning, such as insertion to a certain knuckle of finger 510.

Magnet array 501 establishes (602) an axial magnetic field along the length of finger 510 and a radial magnetic field perpendicular to the length of finger 510. In this example, magnet array 501 comprises an array of permanent magnets, and thus the magnetic fields are constantly established within central hole 502 of magnet array 501. When finger 510 is inserted into central hole 502 of magnet array 501, the magnetic field is thus established in finger 510. In this example, a first magnetic field component, namely axial magnetic field 503, is established simultaneously to a second magnetic field component, namely radial magnetic field 504.

Once finger 510 is inserted into central hole 502 of magnet array 501, magnet array 501 is rotated (603) around finger 510. Since finger 510 is inserted into central hole 502, magnet array 501 is free to rotate about finger 510. The rotation could be effected by a human merely twisting magnet array 501 around finger 510, or could be automated through the use of a motor or servo drive to more precisely control rotation of magnet array 501 around finger 510. In some examples, a positional detection device is employed to track the angular position of magnet array 501 around finger 510. The positional detection device could comprise circuitry and equipment to determine an angular alignment of magnet array 501, such as a rotation gauge, accelerometer, servo feedback mechanism, encoding pins, synchro, or other rotational or positional detection equipment. The positional information could be transferred to processing module 521 over link 570 or another link for processing module 521 to identify optical intensity drive parameters or to determine optical detection times.

Measurement device 520 emits (604) an intensity-modulated optical signal into finger 510 during rotation of the magnet array, where the intensity of the optical signal is synchronized to the rotation of magnet array 501. Processing module 521 determines an intensity of an output drive signal based on at least the rotation angle of magnet array 501 around finger 510. Processing module 521 transfers the output drive signal to drive module 522 which is used to drive laser 524 according to the output signal. Drive module 522 modifies the output intensity of the optical signal produced by laser 524 according to the output signal received from processing module 521. Laser 524 then introduces the intensity modulated optical signal onto optical fiber 571 for emission into finger 510. In other examples, a switching element could be included in drive module 522 to control the output intensity of laser 524, such as an RF switch to enable/disable a drive signal for laser 524. In yet other examples, a switching element could be included after laser 524 to modify the optical intensity of the optical signals output by laser 524, such as an optical switch or optical attenuator.

Optical coupler 560 couples the optical signal of optical fiber 571 into finger 510. In some examples, optical coupler 560 is coupled to magnet array 501 as a single module to apply both magnetic fields and optical signals to finger 510. In other examples, optical coupler 560 is a separate element, and comprises a clamp, adhesive, or band to press optical components of optical coupler 560 onto finger 510. Finger 510 could be inserted into portions of optical coupler 560. In this example, optical coupler 560 emits and detects optical signals near the tip of finger 510. Thus, the optical measurement will occur more near the tip of the finger than where the magnetic fields are applied. A fixed distance between the applied magnetic field and the optical signals could be achieved by a gauge or by including both magnet array 501 and optical coupler 560 in the same enclosure. In further examples, optical coupler 560 could be included or integrated into the central hole of magnet array 501, or could be included in the same enclosure or casing as magnet array 501.

Magnetically sensitive components of finger 510 will react to the changing rotational alignment of magnet array 501. The magnetically sensitive components include erythrocytes in this example, but could include other components of finger 510 in further examples. These erythrocytes will tend to align along the magnetic fields produced by magnet array 501. Since magnet array 501 produces a two-dimensional magnetic field in central hole 502, namely axial field 503 and radial field 504, the erythrocytes will align according to the applied two-dimensional magnetic field. When magnet array 501 is rotated, and thus the applied magnetic field is altered, the erythrocytes will likewise change alignment according to the rotating two-dimensional magnetic field, tending to rotate in accordance with the alignment of radial field 504, with a rotational axis aligned with axial field 503. As the orientation of the fields of magnet array 501 changes, the detected optical intensity at an optical sensor, such as at optical coupler 560, will vary according to the rotation of the fields due to the alignment of the erythrocytes. Thus, the alignment of the erythrocytes will affect the detected optical intensity of emitted optical signals within finger 510. When the magnetic field is in a first orientation to the optical detector, such as in an aligned orientation between the detector and the radial magnetic field, a first optical intensity will be observed. When the magnetic field is in a second orientation to the optical detector, such as in an orthogonal orientation between the detector and the radial magnetic field, a second optical intensity will be observed. Intermediate orientations will have detected optical intensities that vary accordingly.

Measurement device 520 detects (605) characteristics of the optical signal. In this example, the optical signal is detected by detector 525 over link 572. Detector 525 captures light related to the optical signal as transmitted or scattered through finger 510. In some examples, detector 525 comprises a photodetector portion which receives the light collected in optical coupler 560 and transferred over optical fiber 572. Detector 252 converts optical characteristics of the optical signals, such as intensity, amplitude, phase difference (when a reference signal is employed), or other characteristics, into electronic signals. In other examples, optical coupler 560 comprises a photodetector portion to detect the optical signals in finger 510, and optical coupler 560 converts the optical signals into electronic signals for transfer over link 572.

In this example, the optical signal is intensity modulated during application into finger 510 during the rotation of magnet array 501. In some examples, such as shown in graph 700 of FIG. 7, optical detection may be configured to only occur during activation of laser 524. In other examples, such as shown in graph 710 of FIG. 7, optical detection may occur continuously during the rotation of magnet array 501. Other configurations could be employed, including combinations thereof.

Processing module 521 identifies (606) a value of a physiological parameter based on at least the characteristics of the optical signals. Processing module 521 receives digitized versions of the detected optical signals or of the optical characteristics from ADC 523, and processes the digitized versions to determine the physiological parameter. The physiological parameter could include any parameter associated with blood or tissue of finger 510, such as total hemoglobin concentration (tHb), regional oxygen saturation (rSO2), or arterial oxygen saturation (SpO2), among other parameters, including combinations thereof. The characteristics of the optical signals could include an amplitude or intensity of detected optical signals through finger 510. The characteristics could also include a phase delay of optical signals if a reference optical signal is employed. Since a continuous rotation of magnet array 501 is employed in this example, measurements of the characteristics could be taken continuously or at discrete angular positions. The characteristics of the optical signals at each alignment could then be processed to determine the physiological parameter. In some examples, a ratio of the characteristics or associated values for each measured alignment could be processed to determine the value of the physiological parameter. A rotation angle of magnet array 501, or an angular offset between magnet array 501 and optical coupler 560, could also be processed along with the characteristics of the optical signals to determine the value of the physiological parameter.

User interface 526 displays (607) the physiological parameter. In some examples, the physiological parameter is displayed to a user, such as a doctor, nurse, technician, or to the patient undergoing measurement. In other examples, the physiological parameter is transferred to a database or report for storage or archival in medical records of the patient. In yet further examples, a graphical display of the physiological parameter along with other parameters or medical information is displayed on a graphical user interface or display screen. The physiological parameters could be correlated to other physiological parameters, such as pulse, heartbeat, medical statistics, or other information. User interface 526 could also allow an operator of measurement device 520 to initiate a measurement as described herein, and could include commands to initiate rotation of magnet array 501.

Figure 7:
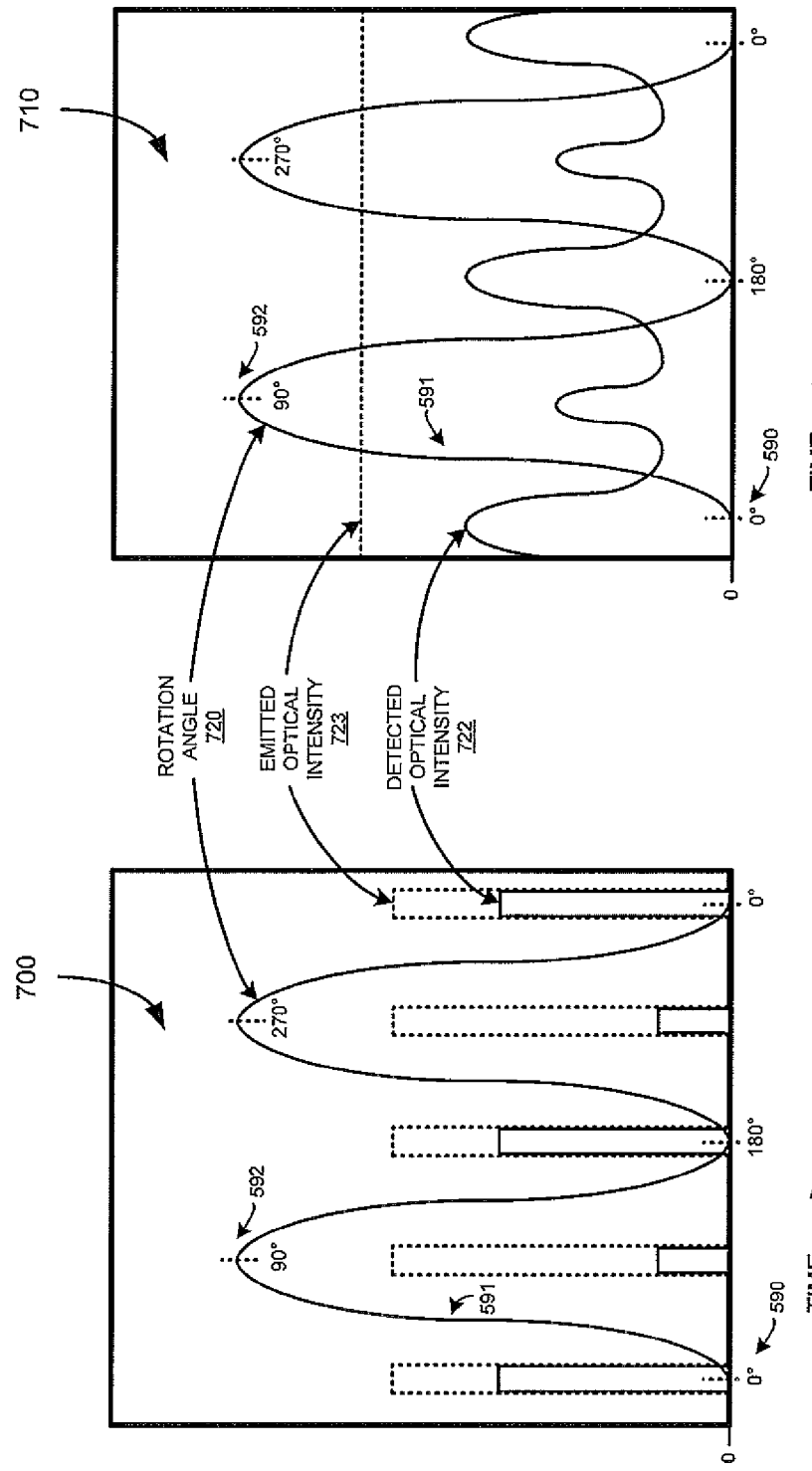
FIG. 7 includes two graphs illustrating example optical intensities with magnetic alignments.

FIG. 7 illustrates two example detected optical intensity modulations based on rotation angle of magnet array 501, namely graph 700 and graph 710. Graph 700 illustrates a square-wave intensity relationship, and graph 710 illustrates a smooth, sinusoidal intensity relationship. It should be understood that the respective amplitudes, waveform widths, duty cycles, and any perceived DC offsets of the waveforms in graphs 700 and 710 are merely used to illustrate the synchronization of rotation angle 720 to detected optical intensity 722. Also, in this example, rotation angle 720 represents a periodic angular offset between optical coupler 560, and magnet array 501. For example, optical coupler 560 could be stationary on finger 510 while magnet array 501 rotates around finger 510. In other examples, magnet array 501 could be stationary on finger 510 and optical coupler 560 could rotate around finger 510.

In a first example, namely graph 700, the optical intensity 722 of a detected optical signal appears synchronized to 0, 90, 180, and 270 degree rotation angles 720 of magnet array 501. In graph 700, the optical intensity is shown in an idealized square waveform. As magnet array 501 is rotated around finger 510, the detected optical intensity will vary according to the rotation angle as shown. Laser 524 could be configured to constantly emit optical signals during the full rotation of magnet array 501. However in graph 700, as shown by emitted optical intensity curve 723, laser 524 is configured to only have an optical output enabled when magnet array 501 is near the 0, 90, 180, and 270 degree rotation angles, and thus the optical output of laser 524 is synchronized to the rotation of magnet array 501. It should be understood that smooth non-square wave optical emissions could instead be employed instead of the square-wave "on/off" intensity as shown in graph 710. Such smooth emission intensities could be employed to create a smooth intensity transition for laser 524 from a low intensity state to a high intensity state, and vice-versa. A sinusoidal intensity modulation of laser 524 could be employed. A ramp-up curve correlated to the exemplary square-wave waveform could instead be employed. This smooth transitioning of the output of laser 524 could aid in reduction of unwanted switching artifacts, or could ensure that laser 524 is always in a lasing condition.

Continuing with graph 700, for a compete rotation of magnet array 501 around finger 510, four instances of optical activation of the optical signals could be performed. Likewise, for a complete rotation of magnet array 501 around finger 510, four main peak optical intensities are detected. Since the optical properties of the aligned magnetically sensitive particles in finger 510 vary with the rotation angle of magnet array 501 due to the direction of the applied magnetic field, a different detected optical intensity 722 is measured for each angular orientation. In graph 700, optical intensity 722 at the 90 and 270 degree orientations is lower than during the 0 and 180 degree orientations, and optical intensity in between the 0, 90, 180, and 270 degree regions is lower than each 0, 90, 180, and 270 degree region. As with graph 710, the actual correlation of rotation angle 720 to optical intensity 722 will vary based on the initial positional relationship between optical coupler 560 and magnet array 501 around finger 510, and thus different waveforms are possible. Also, it should be noted that the maximum detected optical intensity 722 for graph 700 is typically always lower than the emitted optical intensity 723, due to attenuation effects of scattering and absorption by tissue of finger 510.

In a second example, namely graph 710, the optical intensity 722 of a detected optical signal appears aligned to the sinusoidal waveform of the rotation angle 720 of magnet array 501. In graph 700, the optical intensity is shown as a sinusoidal waveform. As magnet array 501 is rotated around finger 510, the detected optical intensity will vary according to the rotation angle as shown. In graph 710, laser 524 is configured to constantly emit optical signals during the full rotation of magnet array 501, as indicated by emitted optical intensity curve 723.

Continuing with graph 710, for a compete rotation of magnet array 501 around finger 510, a smooth transition between maximum intensities and minimum intensities is observed. Likewise, for a complete rotation of magnet array 501 around finger 510, four main peak optical intensities are detected. Since the optical properties of the aligned magnetically sensitive particles in finger 510 vary with the rotation angle of magnet array 501 due to the direction of the applied magnetic field, a different detected optical intensity 722 is measured for each angular configuration in graph 710. In graph 710, detected optical intensity 722 at the 90 and 270 degree orientations is lower than during the 0 and 180 degree orientations, and detected optical intensity in between the 0, 90, 180, and 270 degree regions is lower than each 0, 90, 180, and 270 degree region. The actual correlation of rotation angle 720 to optical intensity 722 will vary based on the initial positional relationship between optical coupler 560 and magnet array 501 around finger 510, and thus different waveforms possible. Also, it should be noted that the maximum detected optical intensity 722 for graph 710 is typically always lower than the emitted optical intensity 723, due to attenuation effects of scattering and absorption by tissue of finger 510.

FIG. 5 includes three exemplary rotation angles of magnet array 501 around finger 510 as indicated by axes 590-592. To better show a correlation between FIG. 5 and FIG. 7, each axis shown in FIG. 5 is labeled onto each of the graphs in FIG. 7. Specifically, a first rotation angle correlated to axis 590 is labeled at the 0 degree point in graphs 700 and 710, a second rotation angle correlated to axis 591 is labeled at an intermediate point between the 0 degree point and the 90 degree point in graphs 700 and 710, and the third rotation angle correlated to axis 592 is labeled at the 90 degree point in graphs 700 and 710. Further rotation angles of magnet array 501 are possible, as shown in graphs 700 and 710. However, only two measurement angles are employed in typical examples, such as at 0 degrees and 90 degrees.

Figure 8:
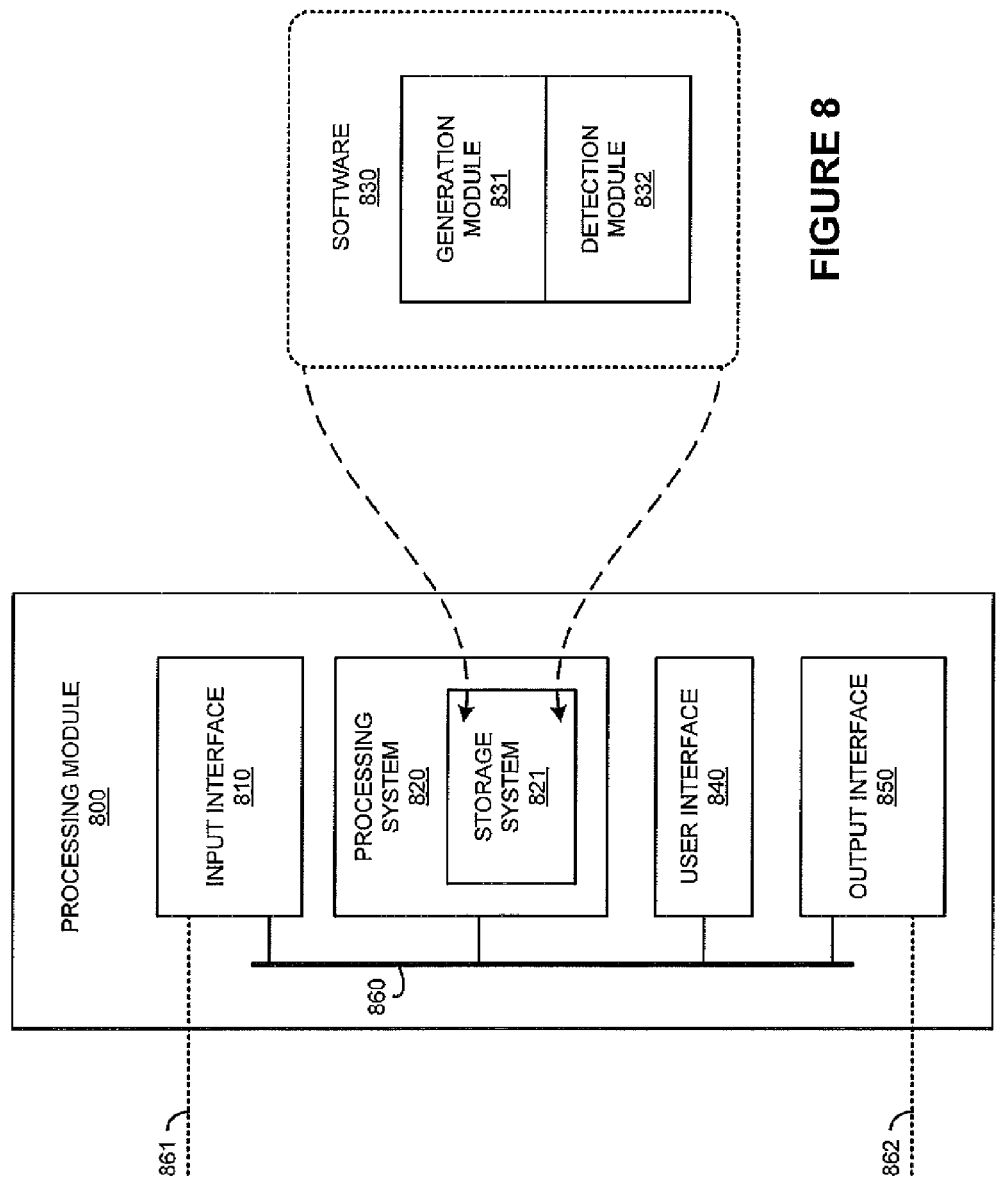
FIG. 8 is a block diagram illustrating a processing module.

FIG. 8 is a block diagram illustrating processing module 800, as an example of processing module 110 found in FIG. 1 or processing module 521 found in FIG. 5, although processing module 110 or processing module 521 could use other configurations. Processing module 800 includes, input interface 810, processing system 820, user interface 840, and output interface 850. Input interface 810, processing system 820, user interface 840, and output interface 850 are shown to communicate over a common bus 860 for illustrative purposes. It should be understood that discrete links could be employed, such as network links or other circuitry. Processing module 800 may be distributed or consolidated among equipment or circuitry that together forms the elements of processing module 800. In some examples, user interface 840 is not included in processing module 800.

Input interface 810 comprises a communication interface for communicating with other circuitry and equipment, such as with transceiver module 120, user interface 526, or ADC 523. Input interface 810 could include transceiver equipment exchanging communications over the associated link 861. It should be understood that input interface 810 could include multiple interfaces, pins, transceivers, or other elements for communicating with multiple external devices. Input interface 810 also receives command and control information and instructions from processing system 820 or user interface 840 for controlling the operations of input interface 810. Link 861 could use various protocols or communication formats as described herein for link 165 or those of measurement device 520, including combinations, variations, or improvements thereof.

Processing system 820 includes storage system 821. Processing system 820 retrieves and executes software 830 from storage system 821. In some examples, processing system 820 is located within the same equipment in which input interface 810, user interface 840, or output interface 850 are located. In further examples, processing system 820 comprises specialized circuitry, and software 830 or storage system 821 could be included in the specialized circuitry to operate processing system 820 as described herein. Storage system 821 could include a non-transitory computer-readable medium such as a disk, tape, integrated circuit, server, flash memory, or some other memory device, and also may be distributed among multiple memory devices.

Software 830 may include an operating system, logs, utilities, drivers, networking software, tables, databases, data structures, and other software typically loaded onto a computer system. Software 830 could contain application programs, server software, firmware, processing algorithms, or some other form of computer-readable processing instructions. When executed by processing system 820, software 830 directs processing system 820 to operate as described herein, such as instruct transceiver modules or drive modules on optical signals for emission into tissue, receive characteristics of optical signals detected in tissue or electrical versions thereof, process the characteristics of the optical signals to determine blood parameters, among other operations.

In this example, software 830 includes generation module 831 and detection module 832. It should be understood that a different configuration could be employed, and individual modules of software 830 could be included in different equipment in processing module 800. Generation module 831 determines parameters for use by a transceiver module or signal synthesis circuitry, such as laser intensity parameters, modulations, laser activation periods, multiplexing parameters, among other operations. Detection module 832 receives receive characteristics of optical signals or electrical versions thereof as detected by external circuitry, and processes the characteristics of the signals to determine blood parameters, among other operations. In some examples, detection module 832 could receive reference signals from other circuitry for processing with the characteristics of the signals.

User interface 840 includes equipment and circuitry to communicate information to a user of processing module 800. Examples of the equipment to communicate information to the user could include displays, indicator lights, lamps, light-emitting diodes, haptic feedback devices, audible signal transducers, speakers, buzzers, alarms, vibration devices, or other indicator equipment, including combinations thereof. The information could include blood parameter information, waveforms, summarized blood parameter information, graphs, charts, processing status, or other information. User interface 840 also includes equipment and circuitry for receiving user input and control, such as for beginning, halting, or changing a measurement process or a calibration process. Examples of the equipment and circuitry for receiving user input and control include push buttons, touch screens, selection knobs, dials, switches, actuators, keys, keyboards, pointer devices, microphones, transducers, potentiometers, non-contact sensing circuitry, or other human-interface equipment.

Output interface 850 comprises a communication interface for communicating with other circuitry and equipment, such as with transceiver module 120, drive module 522, or user interface 312. Output interface 850 could include transceiver equipment exchanging communications over the associated link 862. It should be understood that output interface 850 could include multiple interfaces, pins, transceivers, or other elements for communicating with multiple external devices. Output interface 850 also receives command and control information and instructions from processing system 820 or user interface 840 for controlling the operations of output interface 850. Link 862 could use various protocols or communication formats as described herein for link 165 or those of measurement device 520, including combinations, variations, or improvements thereof.

Bus 860 comprises a physical, logical, or virtual communication link, capable of communicating data, control signals, and communications, along with other information. In some examples, bus 860 is encapsulated within the elements of processing module 800, and may be a software or logical link. In other examples, bus 860 uses various communication media, such as air, space, metal, optical fiber, or some other signal propagation path, including combinations thereof. Bus 860 could be a direct link or might include various equipment, intermediate components, systems, and networks.

Figure 9:
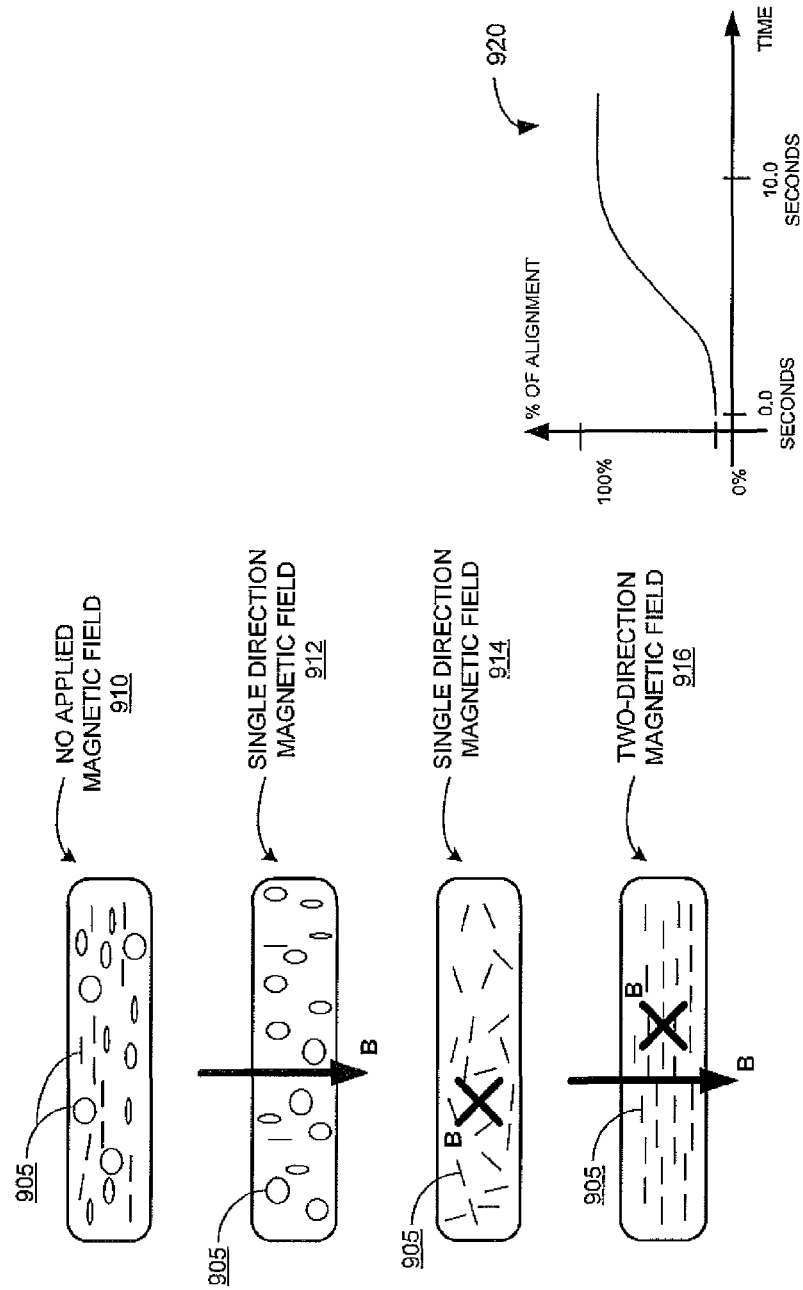
FIG. 9 illustrates example erythrocyte orientations.

FIG. 9 illustrates example erythrocyte orientations. FIG. 9 includes four diagrams, namely 910, 912, 914, and 916. Each of the four diagrams in FIG. 9 includes a representative sample of tissue of a patient, such as tissue 170 of FIG. 1 or finger 510 of FIG. 5, although other configurations could be employed. Also, the representative sample of tissue is merely illustrative of blood particles within tissue, where the tissue could include skin, muscle, venous tissue, marrow, or other tissue of a patient which contains blood. Each of the four diagrams includes red blood cells, namely erythrocytes 905, in various orientations. Erythrocytes 905 comprise a generally flat, round shape, such as a flattened torus. Erythrocytes 905 also comprise hemoglobin molecules which can react to applied magnetic fields.

In the first diagram 910, no magnetic fields are applied within or around the tissue, and consequently, erythrocytes 905 in diagram 910 are randomly ordered and oriented due to blood motions, tissue movement, diffusion, thermal influences, among other factors.

In the second diagram 912, a one-dimensional- or single-direction-magnetic field is applied to the tissue and likewise to erythrocytes 905. In this example, the applied magnetic field is shown as a downward magnetic field. Erythrocytes 905 react to the applied magnetic field in diagram 912 and orient themselves to align edge-on with the magnetic field. However, erythrocytes 905 in diagram 912 can still rotate freely in any angular orientation around this applied magnetic field, and thus are still have randomized orientations in certain directions.

In the third diagram 914, a different one-dimensional- or single-direction-magnetic field is applied to the tissue and likewise to erythrocytes 905. In this example, the applied magnetic field is shown as an inward magnetic field. Erythrocytes 905 react to the applied magnetic field in diagram 914 and orient themselves to align edge-on with the magnetic field. However, erythrocytes 905 in diagram 914 can still rotate freely in any angular orientation around this applied magnetic field, and thus are still have randomized orientations in certain directions.

In the fourth diagram 916, a different two-dimensional- or two-direction-magnetic field is applied to the tissue and likewise to erythrocytes 905. The two-dimensional field could be applied within a central hole of a magnet array as discussed herein. In this example, the applied magnetic field is shown as both an inward magnetic field and a downward magnetic field. The magnetic fields in diagram 916 could correspond to the axial and radial magnetic field components discussed herein. Erythrocytes 905 react to the applied magnetic fields in diagram 916 and orient themselves to align with both magnetic fields. Thus, erythrocytes 905 in diagram 916 are constrained in two directions, and line up in a more orderly fashion than in a one-dimensional applied field. Erythrocytes 905 can still be positionally displaced at random locations within the tissue, but their orientation is highly controlled as shown in diagram 916.

FIG. 9 also includes graph 920. Graph 920 illustrates a typical response curve for erythrocytes to respond to an applied magnetic field. The vertical axis represents the amount of erythrocytes that are aligned with the magnetic field, as a percentage of total erythrocytes. The horizontal axis represents the amount of time that has passed since application of the magnetic field. In this example, graph 920 beings with a time of 0.0 seconds when the magnetic field is applied, and ends at approximately 10 seconds when a measurement is taken for the tissue when a substantial portion of the erythrocytes are aligned. The amount of time for erythrocytes to align is proportional to the strength of the applied magnetic field as well as the depth of the tissue, thus the times shown in graph 920 will vary.

Figure 10:
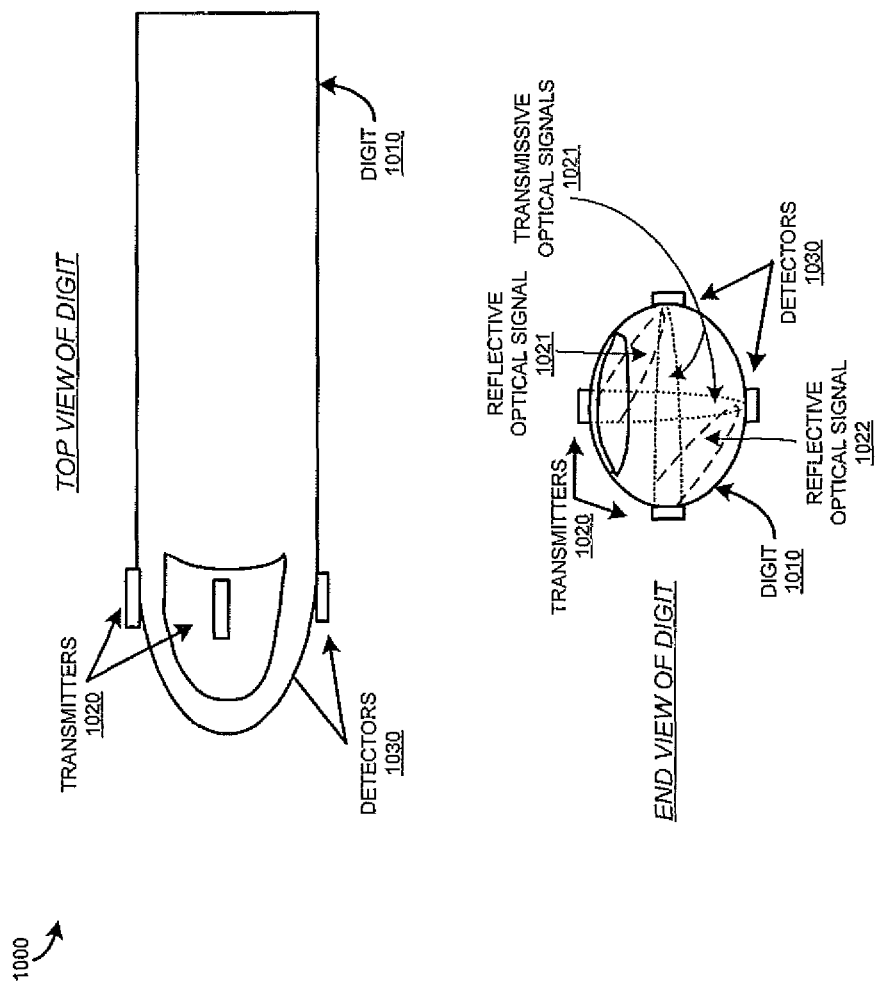
FIG. 10 is a system diagram illustrating a system for measuring a physiological parameter of blood in a patient.

FIG. 10 is presented as a further example of a system for measuring a physiological parameter of blood in a patient. A simplified system 1000 is shown in FIG. 10 to emphasize a further configuration of optical emitters and detectors on a digit of a patient. FIG. 10 includes two views of system 1000, namely the top view of digit 1010 and the end view of digit 1010.

System 1000 includes digit 1010, transmitters 1020, and detectors 1030. Digit 1010 comprises tissue of a patient, such as a finger or toe, or other tissue portion of a patient. Transmitters 1020 could each comprise various optical signal transmission elements, such as optical fibers, prisms, optical waveguides, or could include laser or light-emitting diode emitter components. Detectors 1030 could each comprise optical signal detection elements, such as optical fibers, prisms, optical waveguides, or could include optical sensors such as photodetectors or photomultiplier tubes. Each of transmitters 1020 and detectors 1030 are optically coupled to the tip of digit 1010, and could be coupled to digit 1010 by a compression band, clamp, adhesive, or other coupling device. Transmitters 1020 and detectors 1030 could be further coupled to a measurement system, such as transceiver module 120 and processing module 110 in FIGS. 1 and 2, measurement system 520 in FIG. 5, or processing module 800 in FIG. 8, although other configurations could be employed.

In FIG. 10, a two-dimensional magnetic field is applied to digit 1010, such as discussed herein for various magnetic array configurations. The magnetic elements of system 1000 are omitted for clarity in FIG. 10. However, a first longitudinal magnetic field would be applied along the length of digit 1010, while simultaneously a second transverse magnetic field would be applied across the thickness of digit 1010. As discussed herein, a magnetic array could be applied to digit 1010 to create the two-dimensional magnetic field, which is optionally rotated around digit 1010 in some examples. Since two transmitters 1020 and two detectors 1030 are employed in this example, the applied magnetic field may optionally be applied in only a single first alignment or orientation and not rotated about digit 1010. The magnetic field could also be optionally rotated around digit 1010 for further measurements. Further embodiments of applied magnetic fields are discussed herein.

During application of the two-dimensional magnetic field into digit 1010, transmitters 1020 each emit optical signals into digit 1010 for receipt by detectors 1030. In this example, two transmitters 1020 are coupled to digit 1010 at orthogonal positions to each other, namely on the top and left side of digit 1010 as shown in the end view. Also, two detectors 1030 are coupled to digit 1010 at orthogonal positions to each other, namely on the bottom and right side of digit 1010 as shown in the end view. Optical signals, as indicated by optical signals 1021 and 1022, could be transmitted from both transmitters 1020 during a first alignment of the applied magnetic fields. These optical signals would then be received at each detector 1030 through digit 1010. Further processing systems could be employed to process the detected signals to determine a value of a physiological parameter, as discussed herein for other examples.

Since optical signals emitted by each of transmitters 1020 would diffuse and scatter through digit 1010, detectors 1030 would typically receive optical signals emitted from any of transmitters 1020 through digit 1010. This is shown in FIG. 10 as transmissive optical signals 1021 and reflective optical signals 1022. When optical signals are applied to the same side of the tissue as a detector, a reflection of light is the dominant detection pathway, and thus this technique is referred to as reflective measurement. When optical signals are applied to the opposite side of or significantly displaced along the tissue as the detector, transmission of light is the dominant detection pathway, and thus this technique is referred to as transmissive measurement. Either reflective measurement or transmissive measurement techniques could be applied in system 1000, including combinations thereof.

Therefore, to further aid in discrimination of the optical signals transmitted by each of transmitters 1020 at each of detectors 1030, optical signals from transmitters 1020 could be enabled sequentially, so each detector 1030 can ensure only the optical signal from one transmitter is detected at any given measurement time. In further examples, both transmitters are enabled simultaneously, and the orthogonal relationship between transmitters may allow enough attenuation of the optical signals at the desired detector for proper signal discrimination. In yet further examples, different wavelengths of light are emitted by each of transmitters 1020 and each of detectors 1030 can detect both wavelengths of light and perform optical or electrical filtering to separate the signals of each transmitter.

Although optical signals applied to tissue have been discussed herein, other signals could be applied to tissue during application of a magnetic field. For example, an acoustic signature could be modulated or otherwise affected by the applied magnetic field when hit by an appropriate optical signal which absorbs or reflects off of the desired blood components. In other examples, a fluorescence signature could be modulated or otherwise affected by the applied magnetic field when illuminated by an optical signal.

Also, although optical emitter/detector pairs in FIGS. 1 and 2 as well as optical coupler 560 of FIG. 5 are shown emitting optical signals adjacent to the detection elements, other configurations could be employed. Either reflective measurement or transmissive measurement techniques could be applied to the systems and methods described herein.

Additionally, although some of the examples discussed herein, the magnet array is rotated around tissue, such as a finger, other configurations could be employed. For example, instead of rotating the magnet array around the tissue, the magnet array could remain stationary. Optical components, such as optical emitters and optical detectors could then be rotated around the tissue, similar to how the magnet array is rotated herein. Similar results and measurements could be achieved by rotating the optical elements instead of the magnetic elements.

Referring back to FIGS. 1 and 2, processing module 110 comprises communication interfaces, computer systems, microprocessors, circuitry, non-transient computer-readable media, or other processing devices or software systems, and may be distributed among multiple processing devices. Processing module 110 could be included in the equipment or systems of transceiver module 120, or could be included in separate equipment or systems. Examples of processing module 110 may also include software such as an operating system, logs, utilities, drivers, databases, data structures, processing algorithms, networking software, and other software stored on a non-transient computer-readable medium.

Transceiver module 120 comprises electrical to optical conversion circuitry and equipment, optical modulation equipment, and optical waveguide interface equipment. Transceiver module 120 could include DDS components, CD/DVD laser driver components, function generators, oscillators, or other signal generation components, filters, delay elements, signal conditioning components, such as passive signal conditioning devices, attenuators, filters, and directional couplers, active signal conditioning devices, amplifiers, or frequency converters, including combinations thereof.

Transceiver module 120 could also include switching, multiplexing, or buffering circuitry, such as solid-state switches, RF switches, diodes, or other solid state devices. Transceiver module 120 also includes laser elements such as a laser diode, solid-state laser, or other laser device, along with associated driving circuitry. Optical couplers, cabling, or attachments could be included to optically mate laser elements to link 160. Transceiver module 120 also comprises light detection equipment, optical to electrical conversion circuitry, photon density wave characteristic detection equipment, and analog-to-digital conversion equipment. Transceiver module 120 could include a photodiode, phototransistor, avalanche photodiode (APD), or other optoelectronic sensor, along with associated receiver circuitry such as amplifiers or filters. Transceiver module 120 could also include phase and amplitude detection circuitry and processing elements.

Magnet array 140 comprises an array of permanent magnets bonded together into a configuration to create net observed magnetic fields within a central hole. The permanent magnet could comprise ferromagnetic materials such as iron, nickel, cobalt, or alloys of rare earth metals, including combinations thereof. In some examples, the array of permanent magnets is referred to as a Halbach array, where an array of magnets sums and cancels the various individual magnetic fields for the component magnets to create a controlled and directional net magnetic field. However, typical Halbach arrays only create an observed magnetic field in a single direction, and many configurations of Halbach arrays do not allow insertion of tissue of a patient into the observed magnetic field.

Tissue 170 is a portion of the tissue of a patent undergoing measurement of a physiological blood parameter. It should be understood that tissue 170 could represent a finger, fingertip, toe, earlobe, forehead, or other tissue portion of a patient undergoing physiological parameter measurement. Tissue 170 could comprise muscle, fat, blood, vessels, or other tissue components. The blood portion of tissue 170 could include tissue diffuse blood and arterial or venous blood. In some examples, tissue 170 is a test sample or representative material for calibration or testing of system 100.

Optical links 160-161 each comprise an optical waveguide, and use glass, polymer, air, space, or some other material as the transport media for transmission of light, and could each include multimode fiber (MMF) or single mode fiber (SMF) materials. A sheath or loom could be employed to bundle each of optical links 160-161 together for convenience. One end of each of optical links 160-161 mates with an associated component of system 100, and the other end of each of optical links 160-161 is configured to emit light into tissue 170 or receive light from tissue 170.

Link 165 uses metal, glass, optical, air, space, or some other material as the transport media, and comprises analog, digital, RF, optical, or power signals, including combinations thereof. Link 165 could use various communication protocols or formats, such as Controller Area Network (CAN) bus, Inter-Integrated Circuit (I2C), 1-Wire, Radio Frequency Identification (RFID), optical, circuit-switched, Internet Protocol (IP), Ethernet, wireless, Bluetooth, communication signaling, or some other communication format, including combinations, improvements, or variations thereof. Link 165 could be a direct link or may include intermediate networks, systems, or devices, and could include a logical network link transported over multiple physical links.

Communication links 160-161 and 165 may each include many different signals sharing the same associated link, as represented by the associated lines in FIGS. 1 and 2, comprising channels, forward links, reverse links, user communications, overhead communications, frequencies, wavelengths, carriers, timeslots, spreading codes, logical transportation links, packets, or communication directions.

The included descriptions and drawings depict specific embodiments to teach those skilled in the art how to make and use the best mode. For the purpose of teaching inventive principles, some conventional aspects have been simplified or omitted. Those skilled in the art will appreciate variations from these embodiments that fall within the scope of the invention. Those skilled in the art will also appreciate that the features described above can be combined in various ways to form multiple embodiments. As a result, the invention is not limited to the specific embodiments described above, but only by the claims and their equivalents.

What is claimed is:

1. A system for measuring a physiological parameter of blood in a patient, the system comprising:
    a magnetic array having an opening therein configured to have tissue of the patient inserted therein and simultaneously establish in the tissue an axial magnetic field and a radial magnetic field perpendicular to the axial magnetic field;
    an emitter configured to emit a first optical signal into the tissue during a first angular configuration between the emitter and the magnetic array, and emit a second optical signal into the tissue during a second angular configuration between the emitter and the magnetic array the second angular configuration being different from the first angular configuration;
    a detector configured to detect characteristics of the first optical signal and the second optical signal;
    a user interface; and
    a processing module configured to:
        calculate a differential of the characteristics of the first and the second optical signals;
        identify a value of a physiological parameter from the differential; and
        display the physiological parameter on the user interface.

2. The system of claim 1, wherein the magnetic array comprises a central hole configured to have the tissue of the patent inserted therein, and wherein the axial magnetic field and the radial magnetic field are established within the central hole.

3. The system of claim 1, wherein the physiological parameter comprises a total hemoglobin parameter of the blood of the patient.

4. The system of claim 1, wherein the characteristics of the first optical signal and the second optical signal comprise an amplitude of the first optical signal and the second optical signal after scattering through the tissue.

5. The system of claim 1, wherein the magnetic array comprises a composite array of permanent magnets forming a central hole, wherein the permanent magnets are organized so both the axial magnetic field and the radial magnetic field are observed in the central hole.

6. The system of claim 1, wherein the tissue comprises a digit of the patent, and wherein the digit is inserted to a first distance into a central hole of the magnetic array for application of the axial magnetic field and the radial magnetic field at the first distance along the digit, and wherein the first optical signal and the second optical signal are each applied at a second distance along the digit.

7. The system of claim 1, wherein the first angular configuration between the emitter and the magnetic array is correlated to a first intensity of the first optical signal and a second intensity of the second optical signal, wherein the second angular configuration between the emitter and the magnetic array is correlated to a second intensity of the first optical signal and a first intensity of the second optical signal, and wherein the first intensity is greater than the second intensity.

8. The system of claim 1, wherein the emitter is configured to emit the first optical signal and the second optical signal over an optical fiber into the tissue, and wherein the detector is configured to detect the characteristics of the first optical signal and the second optical signal over optical sensors arranged on the tissue.

9. A method for measuring a physiological parameter of blood in a patient, the method comprising:
    simultaneously establishing within tissue of the patient inserted into a magnetic array an axial magnetic field and a radial magnetic field perpendicular to the axial magnetic field;
    emitting optical signals into the tissue during at least a first angular configuration and a second angular configuration between the magnetic array and the optical signals;
    detecting characteristics of the optical signals at both the first and second angular configurations between the magnetic array and the optical signals;
    identifying a differential using at least the characteristics of the optical signals which vary when measured in the first and second angular configurations between the magnetic array and the optical signals;
    identifying a value of a physiological parameter using the differential; and
    in a user interface, receiving the value of the physiological parameter and displaying the value of the physiological parameter.

10. The method of claim 9, wherein the magnetic array comprises a central hole configured to have the tissue of the patent inserted therein, and wherein the axial magnetic field and the radial magnetic field are established within the central hole.

11. The method of claim 9, wherein the physiological parameter comprises a total hemoglobin parameter of the blood of the patient.

12. The method of claim 9, wherein the characteristics of the optical signals comprise an amplitude of the optical signals after scattering through the tissue.

13. The method of claim 9, wherein the magnetic array comprises a composite array of permanent magnets forming a central hole, wherein the permanent magnets are organized so both the axial magnetic field and the radial magnetic field are observed in the central hole.

14. The method of claim 9, wherein the tissue comprises a digit of the patent, and wherein the digit is inserted to a first distance into a central hole of the magnetic array for application of the axial magnetic field and the radial magnetic field at the first distance along the digit, and wherein the optical signals are applied at a second distance along the digit.

15. The method of claim 9, wherein emitting the optical signals into the tissue comprises emitting a first optical signal into the tissue at a first position and emitting a second optical signal into the tissue at a second position, wherein the first position and the second position are oriented orthogonally along the tissue.

16. The method of claim 9, wherein emitting the optical signals into the tissue comprises emitting the optical signals over optical fibers into the tissue, and wherein detecting the characteristics of the optical signals comprises detecting the characteristics of the optical signals over optical sensors arranged on the tissue.

17. A system for measuring a physiological parameter of blood in a patient, the system comprising:
    a magnetic array comprising an central hole configured to have a digit of the patient inserted therein, the magnetic array configured to simultaneously establish within the central hole a first magnetic field along the length of an inserted digit and a second magnetic field perpendicular to the inserted digit;
    a transceiver module configured to emit a first optical signal into tissue of the digit during an initial alignment of the magnetic array around the inserted digit, and emit a second optical signal into the tissue of the digit during a rotated alignment of the magnetic array around the inserted digit, the rotated alignment being different from the initial alignment;
    the transceiver module configured to detect characteristics of the first optical signal and the second optical signal through the tissue of the digit;
    a processing module configured to:
        identify a differential using at least the characteristics of the first optical signal and the characteristics of the second optical signal which vary when measured in the initial alignment and the rotated alignment of the magnetic array around the inserted digit; and
        identify a value of a physiological parameter using the differential; and
    a user interface configured to receive the value of the physiological parameter and display the value of the physiological parameter.

* * * * *